United States Patent [19]
Valbuena

[11] Patent Number: 5,589,648
[45] Date of Patent: Dec. 31, 1996

[54] TEST KIT GRIPPING APPARATUS

[76] Inventor: Matthew A. Valbuena, 23235 Sky Dr., Lake Forest, Calif. 92630

[21] Appl. No.: 342,216

[22] Filed: Nov. 18, 1994

[51] Int. Cl.⁶ .................................................. G01N 1/12
[52] U.S. Cl. ..................... 73/864.51; 248/312.1
[58] Field of Search ..................... 73/864.51, 864.63; 248/318, 323, 327, 219.3, 229, 274, 316.1, 310, 311.2, 312.1, 314, 176.1

[56]  References Cited

U.S. PATENT DOCUMENTS

| 3,212,743 | 10/1965 | Culver | 248/312.1 |
|---|---|---|---|
| 3,310,270 | 3/1967 | Ciancio | 248/318 |
| 3,960,021 | 6/1976 | Jones | 73/864.51 |
| 4,061,038 | 12/1977 | Clark, Jr. | 73/864.51 |
| 4,454,775 | 6/1984 | Ellis | 73/864.51 |
| 5,442,970 | 8/1995 | Hutchins | 73/864.63 |

FOREIGN PATENT DOCUMENTS

| 237952 | 1/1911 | Germany | 248/312.1 |
|---|---|---|---|
| 362814 | 8/1962 | Switzerland | 248/314 |
| 559678 | 3/1975 | Switzerland | 248/311.2 |
| 762889 | 12/1956 | United Kingdom | 73/864.51 |

Primary Examiner—Robert Raevis
Attorney, Agent, or Firm—Donald E. Stout

[57]  ABSTRACT

A gripping apparatus for a pool or spa water test kit is provided, which comprises a tubular handle element and a retaining bracket adapted to receive and securely grip the water test kit. The gripping apparatus may be used to manipulate the water test kit into any predetermined submerged location within the pool or spa from a remote location spaced from the edge thereof, for the purpose of obtaining one or more water samples. The ability to submerge the test kit into the water from a remote location eliminates the need in the prior art to kneel down at the edge of the pool or spa or to extend one's arm into the water to obtain necessary water samples.

10 Claims, 2 Drawing Sheets

TEST KIT GRIPPING APPARATUS

BACKGROUND OF THE INVENTION

This invention relates to swimming pool and spa maintenance equipment, and more particularly to an apparatus for gripping a water test kit.

While swimming pools and spas afford hours of pleasure, exercise, and relaxation, they also require hours of periodic maintenance in order to preserve healthful and attractive water quality. The required maintenance includes cleaning the pool (i.e. skimming the water surface and vacuuming the bottom), but also includes chemically treating the water to ensure that it remains chemically balanced (e.g. maintains proper chlorine, pH, Total Alkalinity, Calcium Hardness, and bromine levels).

In order to properly treat the water, it is necessary to chemically test it to determine its existing condition. Inexpensive test kits are widely available for this purpose, and typically include a clear plastic housing having a plurality of empty tubes for receiving water samples from the pool or spa. Different test kits are available for testing different chemical levels, but basic commonly available test kits comprise a tube for determining the pH level of the water, and a second tube for determining the chlorine level of the water. Once water samples have been received into each of the tubes, a pH reagent is introduced into the sample in the pH tube and a chlorine reagent is introduced into the sample in the chlorine tube. Then, each tube is capped, and the entire housing is shaken to mix each water sample with its added reagent.

Adjacent to each of the respective tubes is a column having graduated color coded sections corresponding to particular pH or chlorine levels, simulating the possible color range of the column's corresponding water sample after mixing with the reagent. To determine the pH level of the water in the pool, the color of the water sample in the pH tube is compared with the corresponding pH column to find the section of the column most closely matching the color of the sample, and thus the pH level of the sample. A similar matching process is conducted with respect to the chlorine water sample and associated chlorine column.

In order to test the pool water in the manner above described, one must first obtain water samples in the plastic housing tubes of the test kit. Since the kit is designed to be hand-held, this requires users to drop to their hands and knees, roll up their sleeves, and extend the arm holding the test kit into the water. Ideally, the sample is taken from a location several feet deep and as close to the center of the pool as possible, in order to ensure that the sample is representative of the water in the pool. However, this is difficult to do in a large pool, and necessitates reaching one's arm into the water up to the shoulder level. Older people, or those who have bad backs or are otherwise physically disabled, may thus have difficulty obtaining an adequate water sample.

Unfortunately, even for those who are healthy, the inconvenience and unpleasantness involved in conducting such a test procedure, and particularly in obtaining an adequate water sample, causes many people to test their pool or spa too infrequently or not at all, often resulting in deficient water quality. This problem is exacerbated when the weather is cool or inclement, which tends to magnify the discomfort of the person obtaining the water samples. Consequently, the water may become chemically unbalanced and thus appear cloudy and discolored, and may even pose a health risk.

What is needed, therefore, is a better means for collecting a representative water sample from a pool or spa, so that the testing procedure will be simpler and thus more regularly performed by pool or spa owners.

SUMMARY OF THE INVENTION

This invention provides a convenient and versatile means for obtaining water samples from any predetermined location in a body of water such as a pool or spa, without the need to bend over or kneel at the edge of the body of water, or to extend one's arm into the water.

More specifically, a gripping apparatus or extension tool for a water test kit is provided, which comprises a tubular handle element and a retaining bracket which is adapted to receive and securely grip the water test kit. The gripping apparatus may be used to manipulate the water test kit into any predetermined submerged location within a body of water from a remote location spaced from the edge of the body of water, for the purpose of obtaining one or more water samples. The use of the inventive extension tool to submerge the test kit into the water from a remote location eliminates the prior art need to kneel down at the edge of the body of water or to extend one's arm into the water to obtain necessary water samples.

The retaining bracket comprises a base portion and two side arm portions which are adapted to grip opposing sides of the test kit. One optional inventive feature of this bracket is that the base portion is adjustable in length, so that the retaining bracket may be adapted to receive test kits having different sizes and configurations.

Another important optional inventive feature is that the handle element may also be adjustable in length, so that water samples may be obtained from any predetermined location in the body of water.

In another aspect of the invention, a gripping apparatus is provided for a water test kit. The test kit comprises a housing having a base portion, an upper portion, and two side edges. The gripping apparatus comprises a tubular handle element and a retaining bracket which is adapted to receive and securely grip the two side edges of the water test kit. The gripping apparatus may be used to manipulate the water test kit into a predetermined submerged location within a body of water from a remote location spaced from its edge, for the purpose of obtaining one or more water samples.

In yet another aspect of the invention, a method is provided for obtaining water samples in a chemical water test kit (the water test kit comprises a housing including a base portion, an upper portion, and two side edges) from a body of water such as a pool or spa, using a gripping apparatus comprising a tubular handle element and a retaining bracket attached to the handle element. The method comprises the steps of inserting the test kit into the retaining bracket so that it is secured to the handle element, gripping the handle element at an end remote from the test kit, manipulating the test kit into a predetermined submerged position within the body of water, and removing the test kit from the body of water so that the water samples may be tested.

The invention, together with additional features and advantages thereof, may best be understood by reference to the following description taken in conjunction with the accompanying illustrative drawing.

DESCRIPTION OF THE PREFERRED EMBODIMENT

Figure 1:
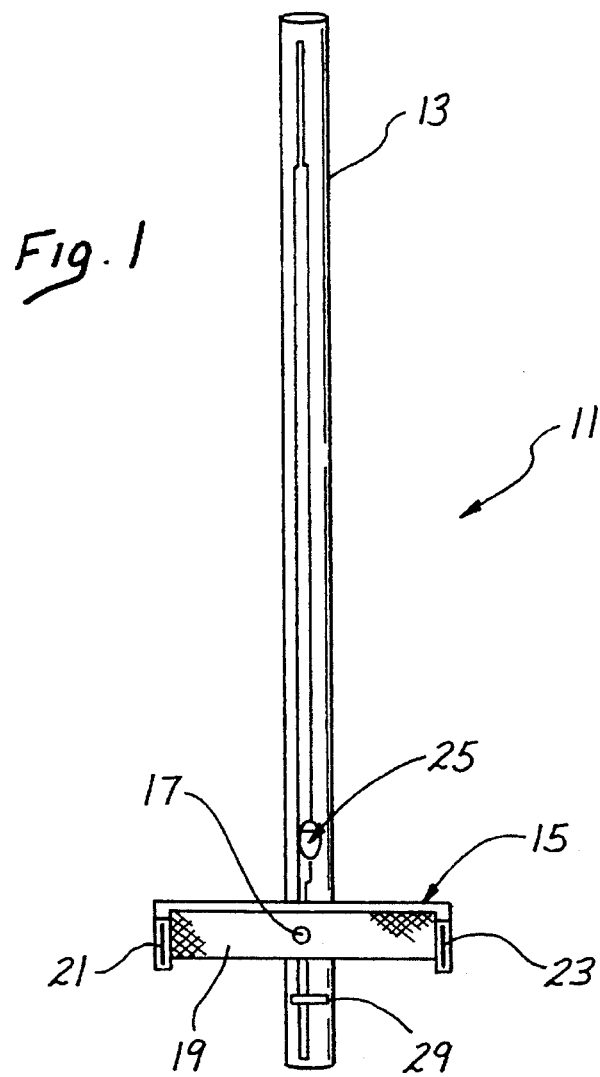
FIG. 1 is a front elevational view illustrating the inventive test kit gripping apparatus.
Figure 4:
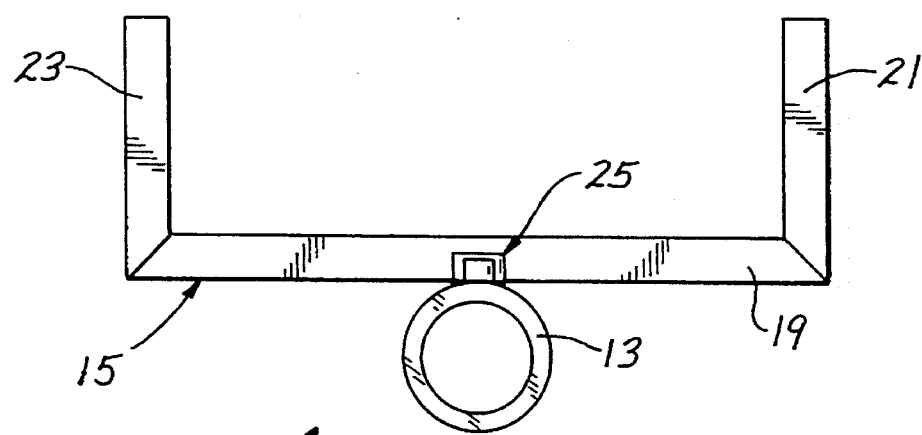
FIG. 4 is a top view of the test kit gripping apparatus illustrated in FIGS. 1–3.
Figure 3:
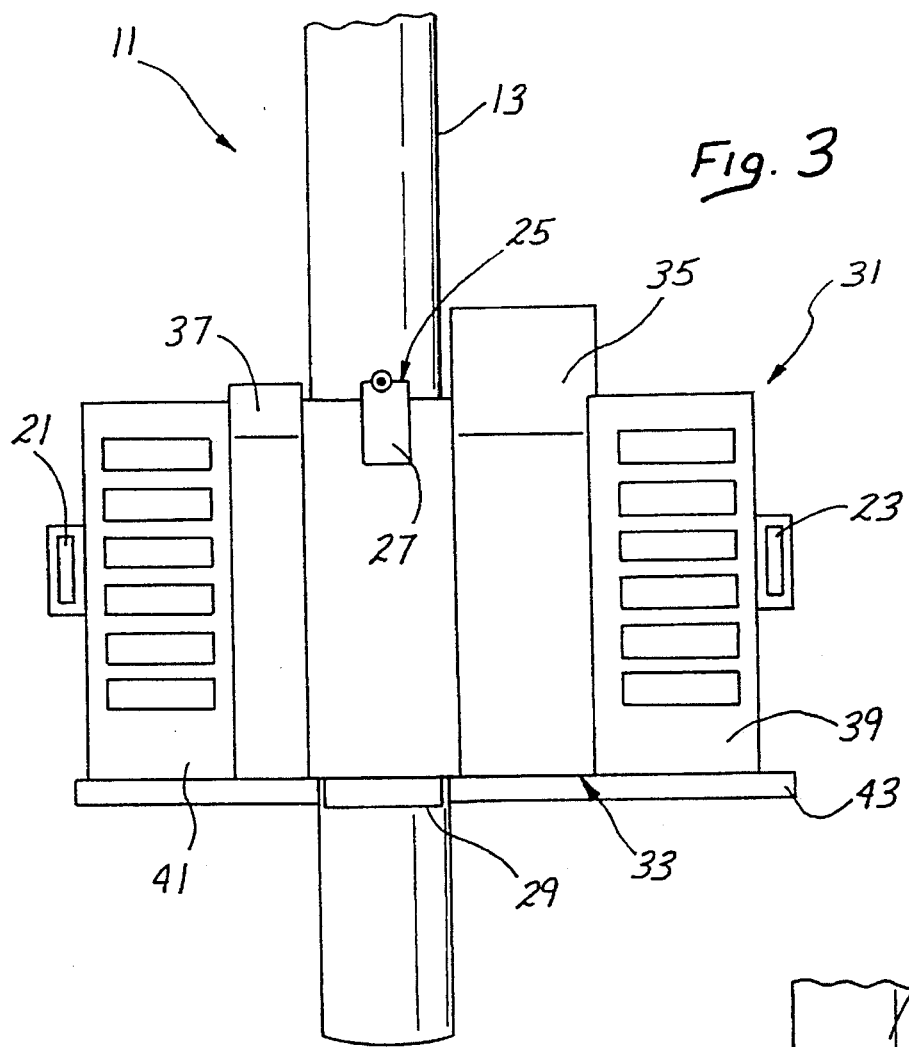
FIG. 3 is a fragmentary enlarged side elevational view of the test kit gripping apparatus illustrated in FIG. 1.

Referring now more particularly to FIGS. 1, 3, and 4, the inventive test kit gripping apparatus or dipper 11 is illustrated. The dipper 11 comprises a tubular handle element 13, which is preferably constructed of aluminum or steel, but may also be fabricated of other materials, such as plastic. A retaining bracket 15 is attached to the lower end of the handle 13, as illustrated, preferably by means of a screw or other mechanical fastener 17, though it may also be bonded using a suitable adhesive or fabricated integrally with the handle 13. The retaining bracket 15 includes a base portion 19 and two side arm portions 21 and 23. Above the retaining bracket on the handle 13 is located a retaining clip 25 which is L-shaped and has a downwardly extending tab 27 spaced radially outwardly from the tubular wall of the handle 13, as best illustrated in FIG. 3. Below the retaining bracket 15 on the tubular wall of the handle 13 is a circumferentially extending slit 29 (FIGS. 2, 3, and 4).

Figure 2:
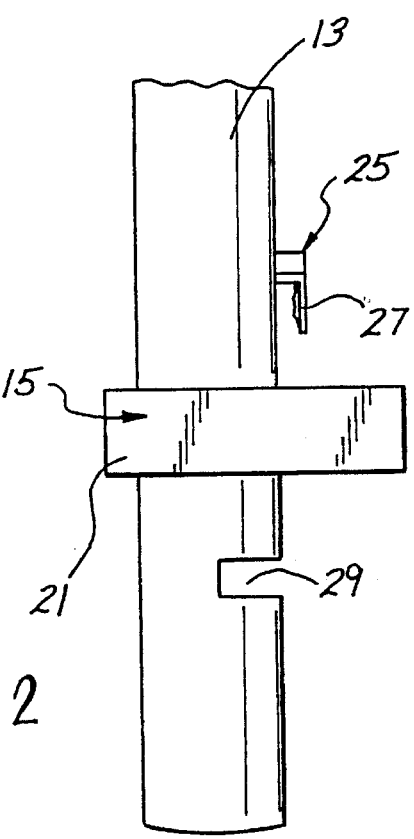
FIG. 2 is a fragmentary enlarged front elevational view of a portion of the apparatus illustrated in FIG. 1, showing the apparatus gripping a chemical test kit for a swimming pool or spa.

The dipper 11 is adapted to securely receive a chemical test kit 31, as shown in FIG. 2, and to permit the test kit to be dipped into the water of the pool or spa to be tested from a remote location away from the edge of the water. The test kit 31 typically comprises a clear plastic housing 33, including a pH (acid demand) test tube 35, a chlorine test tube 37, a first graduated color-coded column 39, calibrated to determine the pH level of the water sample in the test tube 35, and a second graduated color-coded column 41, calibrated to determine the chlorine level of the water sample in the test tube 37, as is well known in the art and described above in the Background of the Invention. Of course, the test kit may vary in structural details, and may be adapted to test for other chemical levels, as desired. The housing 33 is designed to rest in a level position on a base portion 43, which is preferably integrally formed with the remainder of the housing 33.

When it is desired to test the water in a pool or spa, the test kit 31 is installed on the dipper 11, as shown in FIG. 2, by inserting the top of the housing 33, between the tubes 35 and 37 beneath the tab 27 of the retaining clip 25. The housing base portion 43, in turn, is received by the slit 29. To further secure the kit in its mounted position on the handle, the side arm portions 21 and 23, which are adapted to be spaced by a distance equal to that of the width of the test kit housing 33, grip each side of the housing 33, as shown. Once the test kit has been installed, the handle 13 may be manipulated so that the entire retaining bracket 15, including the test kit 31, is submerged into the pool or spa at a desired location, and to a desired depth, thereby filling the test tubes 35 and 37 with water. Then, the handle may be further manipulated to remove the test kit from the water, in an upright position so that the water samples do not spill from the test tubes 35 and 37. The test kit may then be dismounted from the dipper 11, and the chemical test procedure may continue in a manner well known in the art.

Many modifications to the preferred embodiment are possible within the scope of the invention. For example, the handle 13 may be made to a predetermined length in order to access all desired portions of the pool to be tested without the need to bend over or to stoop to one's knees. Alternatively, the handle may be fabricated so that its length is adjustable (ie: with a telescopic configuration). Similarly, the base portion 19 of the retaining bracket 15 may be made to be adjustable in length, so that the spacing between the side arm portions 21 and 23 may vary to adapt to different sized test kits.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A gripping apparatus for a water test kit, said water test kit comprising a housing having a base portion, an upper portion, and two side edges, said gripping apparatus comprising:

a handle element;

a retaining bracket having a base portion and two side arm portions, said side arm portions being adapted to grip said two water test kit side edges;

a slit disposed on said handle element for receiving a base portion of said test kit; and clip means disposed on said handle element above said slit for securing an upper portion of said test kit to said handle element;

wherein said gripping apparatus may be used to manipulate said water test kit into a predetermined submerged location within a body of water for the purpose of obtaining one or more samples of said water.

2. A gripping apparatus as recited in claim 1, wherein said retaining clip is generally L-shaped, having a downwardly extending tab spaced outwardly from the wall of said handle element, said clip being adapted to receive and secure said test kit upper portion within the space between said tab and said handle element wall.

3. A gripping apparatus as recited in claim 1, wherein said retaining bracket is adjustable in order to receive test kits having different sizes and configurations.

4. A gripping apparatus as recited in claim 3, wherein the base portion of said retaining bracket is adjustable in length.

5. A gripping apparatus as recited in claim 1, wherein said handle element is tubular.

6. A gripping apparatus as recited in claim 5, wherein said slit extends circumferentially about the tubular wall of said handle element.

7. A gripping apparatus as recited in claim 1, wherein the length of said handle element is adjustable.

8. A gripping apparatus for a water test kit, said water test kit comprising a housing having a base portion, an upper portion, and two side edges, said gripping apparatus comprising:

a tubular handle element having a tubular wall;

a retaining bracket having a base portion and two side arm portions, said side arm portions being adapted to grip said two water test kit side edges; and a slit disposed on said handle element and extending circumferentially about the tubular wall of the handle element for receiving a base portion of said test kit; and wherein said gripping apparatus may be used to manipulate said water test kit into a predetermined submerged location within a body of water for the purpose of obtaining one or more samples of said water.

9. A gripping apparatus as recited in claim 8 and further including a retaining means disposed on said handle element above said slit for securing an upper portion of said test kit to said handle element.

10. A gripping apparatus for a water test kit, said water test kit comprising a housing having a base portion, an upper portion, and two side edges, said gripping apparatus comprising:

a tubular handle element having an adjustable length;

a retaining bracket having a base portion and two side arm portions, said side arm portions being adapted to grip said two water test kit side edges;

a slit located on said handle element for receiving a base portion of said test kit; and a retaining clip located on said handle element above said slit for securing an upper portion of said test kit to said handle element;

wherein said gripping apparatus may be used to manipulate said water test kit into a predetermined submerged location within a body of water for the purpose of obtaining one or more samples of said water.

\* \* \* \* \*